(12) United States Patent
Mochizuki

(10) Patent No.: US 9,878,617 B2
(45) Date of Patent: Jan. 30, 2018

(54) SAFE DRIVING MANAGEMENT SYSTEM, SLEEP SHORTAGE DETERMINATION DEVICE, SLEEP DATA MEASUREMENT DEVICE, USER IDENTIFICATION INFORMATION INPUT DEVICE, CONTROL METHOD AND STORAGE MEDIUM

(71) Applicant: TANITA CORPORATION, Tokyo (JP)

(72) Inventor: Kei Mochizuki, Tokyo (JP)

(73) Assignee: TANITA CORPORATION, Itabashi-ku, Tokyo (JP)

( * ) Notice: Subject to any disclaimer, the term of this patent is extended or adjusted under 35 U.S.C. 154(b) by 0 days.

(21) Appl. No.: 14/965,929

(22) Filed: Dec. 11, 2015

(65) Prior Publication Data

US 2016/0193918 A1 Jul. 7, 2016

(30) Foreign Application Priority Data

Dec. 26, 2014 (JP) ................. 2014-264095

(51) Int. Cl.
*B60K 28/06* (2006.01)
*A61B 5/00* (2006.01)
*A61B 5/18* (2006.01)
*A61B 5/024* (2006.01)
*A61B 5/08* (2006.01)
*A61B 5/11* (2006.01)

(52) U.S. Cl.
CPC .............. *B60K 28/06* (2013.01); *A61B 5/024* (2013.01); *A61B 5/0816* (2013.01); *A61B 5/11* (2013.01); *A61B 5/18* (2013.01); *A61B 5/4809* (2013.01); *A61B 5/7246* (2013.01)

(58) Field of Classification Search
CPC ......... A61B 5/024; A61B 5/18; A61B 5/0816; A61B 5/11; B60K 28/02; B60K 28/06
USPC .......................................... 340/576
See application file for complete search history.

(56) References Cited

U.S. PATENT DOCUMENTS

| 6,927,694 B1* | 8/2005 | Smith | B60K 28/066 340/573.1 |
| 2007/0296601 A1* | 12/2007 | Sultan | A61B 5/18 340/576 |
| 2009/0318776 A1* | 12/2009 | Toda | A61B 5/18 600/301 |
| 2010/0030434 A1* | 2/2010 | Okabe | A61B 5/165 701/48 |

(Continued)

FOREIGN PATENT DOCUMENTS

JP 2006-31058 A 2/2006

*Primary Examiner* — Omar Casillashernandez
(74) *Attorney, Agent, or Firm* — Sughrue Mion, PLLC

(57) ABSTRACT

A safe driving management system comprises: a sleep data measurement device; a sleep shortage determination device; and a user identification information input device, wherein the sleep shortage determination device has a sleep shortage determination unit configured to compare sleep data of a case where a driver's sleep is sufficient and acquired data within predetermined duration containing identical data to the sleep data measured within the predetermined duration in the past from when the driver boards a vehicle to start driving, and to determine that the driver is in sleep shortage, when a difference between the sleep data and the acquired data within the predetermined duration is equal or greater than a predetermined difference.

7 Claims, 8 Drawing Sheets

(56) References Cited

U.S. PATENT DOCUMENTS

| | | | | |
|---|---|---|---|---|
| 2011/0109462 A1* | 5/2011 | Deng | .................... | G08B 21/06 340/575 |
| 2012/0165622 A1* | 6/2012 | Rodr guez Ib nez | .... | A61B 5/00 600/301 |
| 2015/0035643 A1* | 2/2015 | Kursun | .............. | G07C 9/00158 340/5.52 |

* cited by examiner

FIG. 5

TBL1

| DATA | SLEEP DATA | | | SLEEPING USER IDENTIFICATION INFORMATION ACQUISITION UNIT | | | | | | | | SUFFICIENT SLEEP FLAG | DETERMINATION FLAG |
|---|---|---|---|---|---|---|---|---|---|---|---|---|---|
| | TIME | RESPIRATION | PULSE | BLOOD PRESSURE | BODY TEMPERATURE | BODY WEIGHT | BODY COMPOSITION | BODY MASS INDEX | BIOELECTRICAL IMPEDANCE | ACETONE CONCENTRATION IN EXHALED GAS | | | |
| DATA 1 | TIME DATA 1 | RESPIRATION DATA 1 | PULSE DATA 1 | BLOOD PRESSURE DATA 1 | BODY TEMPERATURE DATA 1 | BODY WEIGHT DATA 1 | BODY COMPOSITION DATA 1 | BODY MASS INDEX DATA 1 | BIOELECTRICAL IMPEDANCE DATA 1 | ACETONE CONCENTRATION IN EXHALED GAS DATA 1 | | 1 | 1 |
| DATA 2 | TIME DATA 2 | RESPIRATION DATA 2 | PULSE DATA 2 | BLOOD PRESSURE DATA 2 | BODY TEMPERATURE DATA 2 | BODY WEIGHT DATA 2 | BODY COMPOSITION DATA 2 | BODY MASS INDEX DATA 2 | BIOELECTRICAL IMPEDANCE DATA 2 | ACETONE CONCENTRATION IN EXHALED GAS DATA 2 | | | |
| DATA 3 | TIME DATA 3 | RESPIRATION DATA 3 | PULSE DATA 3 | BLOOD PRESSURE DATA 3 | BODY TEMPERATURE DATA 3 | BODY WEIGHT DATA 3 | BODY COMPOSITION DATA 3 | BODY MASS INDEX DATA 3 | BIOELECTRICAL IMPEDANCE DATA 3 | ACETONE CONCENTRATION IN EXHALED GAS DATA 3 | | 1 | |
| DATA 4 | TIME DATA 4 | RESPIRATION DATA 4 | PULSE DATA 4 | BLOOD PRESSURE DATA 4 | BODY TEMPERATURE DATA 4 | BODY WEIGHT DATA 4 | BODY COMPOSITION DATA 4 | BODY MASS INDEX DATA 4 | BIOELECTRICAL IMPEDANCE DATA 4 | ACETONE CONCENTRATION IN EXHALED GAS DATA 4 | | 1 | |
| DATA 5 | TIME DATA 5 | RESPIRATION DATA 5 | PULSE DATA 5 | BLOOD PRESSURE DATA 5 | BODY TEMPERATURE DATA 5 | BODY WEIGHT DATA 5 | BODY COMPOSITION DATA 5 | BODY MASS INDEX DATA 5 | BIOELECTRICAL IMPEDANCE DATA 5 | ACETONE CONCENTRATION IN EXHALED GAS DATA 5 | | | |
| ... | ... | ... | ... | ... | ... | ... | ... | ... | ... | ... | ... | ... | ... |

SAFE DRIVING MANAGEMENT SYSTEM, SLEEP SHORTAGE DETERMINATION DEVICE, SLEEP DATA MEASUREMENT DEVICE, USER IDENTIFICATION INFORMATION INPUT DEVICE, CONTROL METHOD AND STORAGE MEDIUM

CROSS-REFERENCE TO RELATED APPLICATION

Priority is claimed on Japanese Patent Application No. 2014-264095, filed on Dec. 26, 2014, the contents of which are incorporated herein by reference.

BACKGROUND

Field of the Invention

The present invention relates to a safe driving management system, a sleep shortage determination device, a sleep data measurement device, a user identification information input device, a control method and a storage medium.

Background

In a case where a driver drives a vehicle such as an automobile and has not obtained a sufficient amount of sleep, there is a possibility that the driver may cause a large accident due to lack of concentration, being drowsy, etc.

Japanese Patent Application, Publication No. 2006-31058 discloses, as related art, a drowsiness alarm device. The device is configured to confirm an awake state of an operator by clicking a switch operable by the operator repeatedly with a few second intervals, and configured to determine that the operator becomes drowsy based on a disruption in clicking, and to emit alarm.

SUMMARY

However, the technology disclosed in Japanese Patent Application, Publication No. 2006-31058 still makes it possible to drive a vehicle even in a case of sleep shortage (a state where sleep is not enough). Furthermore, in addition to the driving operation, another operation for drowsiness detection is necessary during driving.

Therefore, a technology capable of determining sleep shortage before a user drives a vehicle has been desired.

An aspect of the present invention is aimed at providing a safe driving management system, a sleep shortage determination device, a sleep data measurement device, a user identification information input device, a control method and a program, that solve the above-mentioned problems.

A first aspect is a safe driving management system, comprising: a sleep data measurement device; a sleep shortage determination device; and a user identification information input device, wherein the sleep shortage determination device has a sleep shortage determination unit configured to compare sleep data of a case where a driver's sleep is sufficient and acquired data within predetermined duration containing identical data to the sleep data measured within the predetermined duration in the past from when the driver boards a vehicle to start driving, and to determine that the driver is in sleep shortage, when a difference between the sleep data and the acquired data within predetermined duration is equal or greater than a predetermined difference.

A second aspect is the safe driving management system, wherein the sleep data measurement device has a sleeping user identification information acquisition unit configured to identify the driver based on measurement information of a body of the driver when acquiring sleep data of the driver, and wherein the user identification information input device has a driving user identification information acquisition unit configured to identify the driver based on the same sort of measurement information of the body as the measurement information of the body, when the driver drives a vehicle.

A third aspect is the safe driving management system, wherein the user identification information input device has a control unit configured to control the vehicle so that the driver cannot drive the vehicle, in a case where the sleep shortage determination unit determines that the driver is in sleep shortage.

A fourth aspect is the safe driving management system, wherein the user identification information input device has the sleep shortage determination unit.

A fifth aspect is a sleep shortage determination device, comprising: a sleep shortage determination unit configured to compare sleep data of a case where a driver's sleep is sufficient and acquired data within predetermined duration containing identical data to the sleep data measured within the predetermined duration in the past from when the driver boards a vehicle to start driving, and to determine that the driver is in sleep shortage, when a difference between the sleep data and the acquired data within predetermined duration is equal or greater than a predetermined difference.

A sixth aspect is a sleep data measurement device, comprising: a sleeping user identification information acquisition unit configured to identify a driver based on measurement information of a body of the driver, when acquiring sleep data of the driver.

A seventh aspect is a user identification information input device, comprising: a driving user identification information acquisition unit configured to identify a driver based on the same sort of measurement information of a body of the driver as the measurement information of the body, when the driver drives a vehicle.

A eighth aspect is a control method of a safe driving management system, the safe driving management system comprising: a sleep data measurement device; a sleep shortage determination device; and a user identification information input device, wherein, in the sleep shortage determination device, a sleep shortage determination unit is configured to compare sleep data of a case where a driver's sleep is sufficient and acquired data within predetermined duration containing identical data to the sleep data measured within the predetermined duration in the past from when the driver boards a vehicle to start driving, and to determine that the driver is in sleep shortage, when a difference between the sleep data and the acquired data within predetermined duration is equal or greater than a predetermined difference.

A ninth aspect is a control method, wherein a sleep shortage determination unit is configured to compare sleep data of a case where a driver's sleep is sufficient and acquired data within predetermined duration containing identical data to the sleep data measured in predetermined duration in the past from when the driver boards a vehicle to start driving, and to determine that the driver is in sleep shortage, when a difference between the sleep data and the acquired data within predetermined duration is equal or greater than a predetermined difference.

A tenth aspect is a control method, wherein a sleeping user identification information acquisition unit configured to identify a driver based on measurement information of a body of the driver, when acquiring sleep data of the driver.

A eleventh aspect is a control method, wherein a driving user identification information acquisition unit configured to identify a driver based on the same sort of measurement information of a body of the driver as the measurement information of the body, when the driver drives a vehicle.

A twelfth aspect is a storage medium that stores a program configured to cause a computer to function as a sleep shortage determination means configured to compare sleep data of a case where a driver's sleep is sufficient and acquired data within predetermined duration containing identical data to the sleep data measured in predetermined duration in the past from when the driver boards a vehicle to start driving, and to determine that the driver is in sleep shortage, when a difference between the sleep data and the acquired data within predetermined duration is equal or greater than a predetermined difference.

A thirteenth aspect is a storage medium that stores a program configured to cause a computer to function as a sleeping user identification information acquisition means configured to identify a driver based on measurement information of a body of the driver, when acquiring sleep data of the driver.

A fourteenth aspect is a storage medium that stores a program configured to cause a computer to function as a driving user identification information acquisition unit configured to identify a driver based on the same sort of measurement information of a body of the driver as the measurement information of the body, when the driver drives a vehicle.

According to the present invention, it is possible to determine sleep shortage before a user drives a vehicle.

BRIEF DESCRIPTION OF THE DRAWINGS

FIG. 5 is a diagram showing an example of data stored by a memory unit included in the server according to the present embodiment.

DESCRIPTION OF THE EMBODIMENTS

First, a configuration of a safe driving management system according to an embodiment of the present invention will be described.

Figure 1:
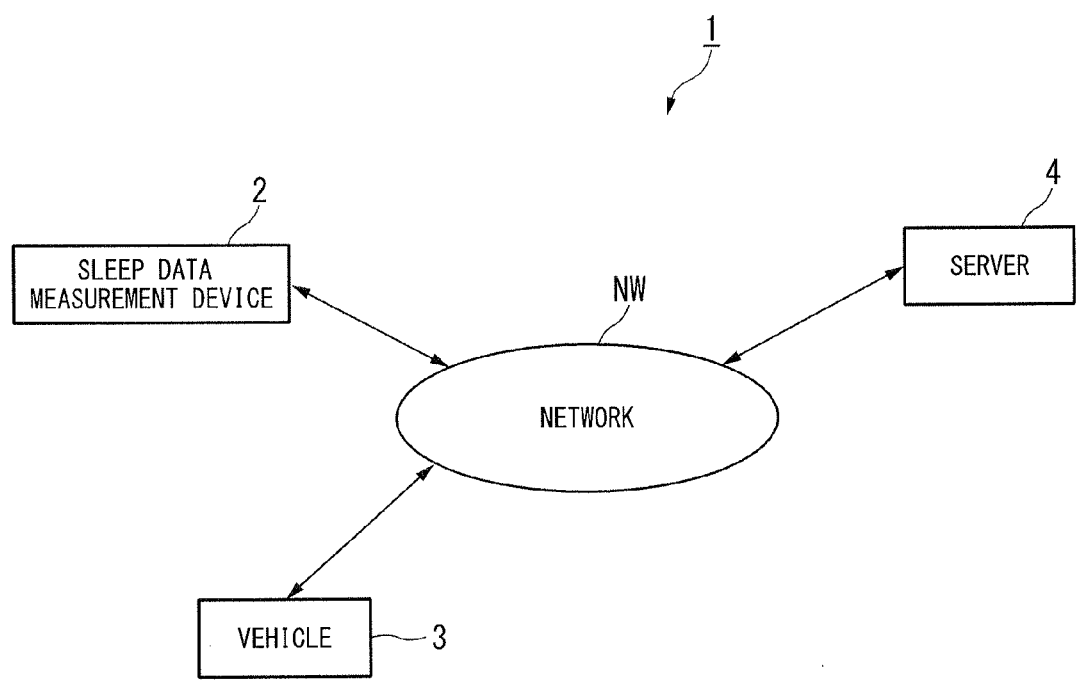
FIG. 1 is a diagram showing an example of a configuration of a safe driving management system according to a present embodiment.

FIG. 1 is a diagram showing an example of the configuration of the safe driving management system according to the present embodiment.

A safe driving management system 1 includes a sleep data measurement device 2, a vehicle 3, a server 4, and a network NW.

The sleep data measurement device 2 included in the safe driving management system 1 measures data of a user during sleep such as pulse, respiration, body motion etc. (hereinafter "sleep data"). When measuring the sleep data of the user, the sleep data measurement device 2 also measures, for example, blood pressure, body temperature, body weight, body composition (body fat, visceral fat, subcutaneous fat, muscle, bone, body water and other components within the body), body mass index, bioelectrical impedance, acetone concentration in exhaled gas etc. as sleeping user identification information for identifying the user (hereinafter "sleeping user identification information").

The vehicle 3 inquires the server 4 about whether or not the user is in a state capable of driving the vehicle 3 before the user drives the vehicle 3.

The server 4 associates an initial sleep data in which the user's sleep is sufficient for driving the vehicle 3 with the sleeping user identification information. Then, the server 4 stores the initial sleep data and the sleeping user identification information in a data table together with a sufficient sleep flag indicating sufficient sleep data and a determination flag indicating that the initial sleep data and the sleeping user identification information are used as determination criteria when analyzing the sleep state. The sleep data are, for example, data indicating a number of respirations, pulse and pulse strength.

Every time the server 4 receives the sleep data of the user and the sleeping user identification information via the network NW, the server 4 compares the sufficient sleep data stored together with the determination flag and the sleep data of the user measured by the sleep data measurement device 2, and analyzes the sleep status of the user measured by the sleep data measurement device 2. For example, the server 4 compares the number of respirations per unit of time, the number of pulses and the strength of pulse contained in the sufficient sleep data stored together with the determination flag and a number of respirations per unit of time, a number of pulses and strength of pulse contained in the sleep data of the user's each sleep respectively. Then, in a case where the server 4 determines the number of respirations per unit of time, the number of pulses and the strength of pulse contained in the sufficient sleep data and the number of respirations per unit of time, the number of pulses and strength of pulse contained in the sleep data of the user's each sleep are identical respectively, the server 4 determines that the user's sleep is sufficient. More specifically, the server 4 subtracts the number of respirations per unit of time contained in the sleep data of the user's each sleep from the number of respirations per unit of time contained in the sufficient sleep data. The server 4 compares a number of respirations subtraction result which is a subtraction result of the aforementioned number of respirations (hereinafter "number of respirations subtraction result"), to a number of respirations threshold value which is preset to determine that the number of respirations per unit of time contained in the sufficient sleep data and the number of respirations per unit of time contained in the sleep data of the user's each sleep are identical (hereinafter "number of respirations threshold value"). In case the number of respirations subtraction result is smaller than the number of respirations threshold value, the server 4 determines that the number of respirations per unit of time contained in the sleep data is identical to the number of respirations per unit of time contained in the sufficient sleep data. Also, the server 4 subtracts the number of pulses per unit of time contained in the sleep data of the user's each sleep from the number of pulses per unit of time contained in the sufficient sleep data. The server 4 compares a number of pulses subtraction result which is a subtraction result of the aforementioned number of pulses (hereinafter "number of pulses subtraction result"), to a number of pulses threshold value which is preset to determine that the number of pulses per unit of time contained in the sufficient sleep data and the number of pulses per unit of time contained in the sleep data of each sleep of the user are identical (hereinafter "number of pulses threshold value"). In case the number of pulses subtraction result is smaller than the number of pulses threshold value, the server 4 determines that the number of pulses per unit of time contained in the sleep data is identical to the number of pulses per unit of time contained in the sleep sufficient data. Also, the server 4 subtract the strength of pulse contained in the sleep data of the user's each sleep from the strength of pulse contained in the sufficient sleep data. The server 4 compares a strength of pulse subtraction result which is a subtraction result of the aforementioned strength of pulse (hereinafter "strength of pulse subtraction result"), to a strength of pulse threshold value which is preset to determine that the strength of pulse contained in the sufficient sleep data and the strength of pulse contained in the sleep data of the user's each sleep are identical (hereinafter "strength of pulse threshold value"). In case the strength of pulse subtraction result is smaller than the strength of pulse threshold value, the server 4 determines that the strength of pulse contained in the sleep data is identical to the strength of pulse contained in the sufficient sleep data. And then, in case the server 4 determines all of the number of respirations per unit of time, the number of pulses per unit of time and the strength of pulse contained in the sufficient sleep data and the number of respirations per unit of time, the number of pulses per unit of time and strength of pulse contained in the sleep data of each time of user's sleep are identical respectively, the server 4 determines that the user's sleep is sufficient. Also, in case the server 4 determines that any of the number of respirations per unit of time, the number of pulses per unit of time and the strength of pulse contained in the sufficient sleep data and the number of respirations per unit of time, the number of pulses per unit of time and strength of pulse contained in the sleep data of the user's each sleep is not identical to each other, the server 4 determines that the user's sleep is not sufficient. In addition, the server 4 may use a number of turning over in bed based on body motions per unit of time to determine whether the user's sleep is sufficient or not. In such a case, if the number of turning over per unit of time is small, the server 4 determines that the user's sleep is sufficient. If the number of turning over per unit of time is large, the server 4 determines that the user's sleep is not sufficient.

The server 4 stores the sleep data in which the user's sleep is determined to be sufficient in the data table together with the sufficient sleep flag.

Furthermore, the server 4 determines whether the user's sleep right before driving the vehicle 3 is sufficient or not by the sleep data with the determination flag as determination criteria. The server 4 transmits the determination result of whether the user's sleep for driving the vehicle 3 is sufficient or not via the network NW to the vehicle 3.

Next, an overview of a process of the safe driving management system 1 according to an embodiment of the present invention will be described.

In the safe driving management system 1, the sleep data measurement device 2 measures the sleep data of the user. Also, when measuring the sleep data of the user, the sleep data measurement device 2 measures the sleeping user identification information for identifying the user. Also, the sleep data measurement device 2 transmits both the sleep data of the user and the sleeping user identification information that is measured to the server 4 via network NW.

The server 4 receives the sleep data of the user and the sleeping user identification information via the network NW from the sleep data measurement device 2. And, the server 4 compares the sleep data of the user and the sleeping user identification information, to the sufficient sleep data of the user stored in the data table together with the determination flag and the sufficient sleep flag, and analyzes whether the user's sleep is sufficient or not. Every time upon receiving the sleep data of the user and the sleeping user identification information via the network NW from the sleep data measurement device 2, the server 4 analyzes whether the user's sleep is sufficient or not. Also, in a case where the user's sleep is sufficient as a result of analyzing the sleeping status, the server 4 stores the sleep data and the sleeping user identification information of the user together with the sufficient sleep flag.

After that, the user sits on the driver seat of the vehicle 3 (boards the vehicle 3) as a driver. Then, when the user drives the vehicle 3, the vehicle 3 measures driving user identification information, which is the same sort of user identification information as the sleeping user identification information (hereinafter "driving user identification information"). And the vehicle 3 transmits the driving user identification information to the server 4 via the network NW.

Upon receiving the driving user identification information via the network NW from the vehicle 3, the server 4 compares the driving user identification information received and the sleeping user identification information stored by each user in the data table. And the server 4 identifies the sleeping user identification information which is identical to the driving user identification information. For example, the server 4 compares blood pressure contained in the driving user identification information and blood pressure contained in each of the sleeping user identification information stored in a memory unit 303 in orderly manner, and identifies the sleeping user identification information containing the blood pressure which is nearest value to the blood pressure contained in the driving user identification information. By this identification, the server 4 resulted in identifying the data table containing the sleep data corresponding to the user boarded the vehicle 3.

The server 4 identifies the sleep data of the user within predetermined duration from present in the past (hereinafter "acquired data within predetermined duration"), among stored data associated with identified sleeping user identification information. For example, among stored data associated with the sleeping user identification information, the server 4 identifies the sleep data within 24 hours from present in the past as acquired data within predetermined duration.

Among the acquired data within predetermined duration, the server 4 identifies the sleep data stored together with the sufficient sleep flag. And the server 4 determines whether the user's sleep within the predetermined duration from present in the past is sufficient for driving the vehicle 3 or not. For example, in a case where the total of the sleep time in the sleep data with a sufficient sleep flag in the acquired data within predetermined duration is 8 hours or more, the server 4 determines that the user's sleep is sufficient for driving vehicle 3. Also, in a case where the total of the sleep time in the sleep data with sleep sufficient flag in the acquired data within predetermined duration is less than 8 hours, the server 4 determines that the sleep of the user is insufficient for driving vehicle 3.

The server 4 transmits the determination result of whether the user's sleep is sufficient for driving the vehicle 3 or not to the vehicle 3 via the network NW.

Upon receiving the determination result of whether the user is in sleep shortage or not from the server 4 via the network NW, the vehicle 3 controls whether or not to allow the user drive as the driver based on the determination result received. For example, in a case where the vehicle 3 receives the determination result from the server 4 via the network NW indicating that the user is in sleep shortage, the vehicle 3 controls not to allow the engine start. Also, the vehicle 3 encourages the user to take a short sleep by an alarm device with a display unit, a vibration device, or speakers etc.

Next, each configuration of the sleep data measurement device 2, the vehicle 3, the server 4 and the network NW included in the safe driving management system 1 according to the present embodiment will be described.

First, a configuration of the sleep data measurement device according to the present embodiment will be described.

Figure 2:
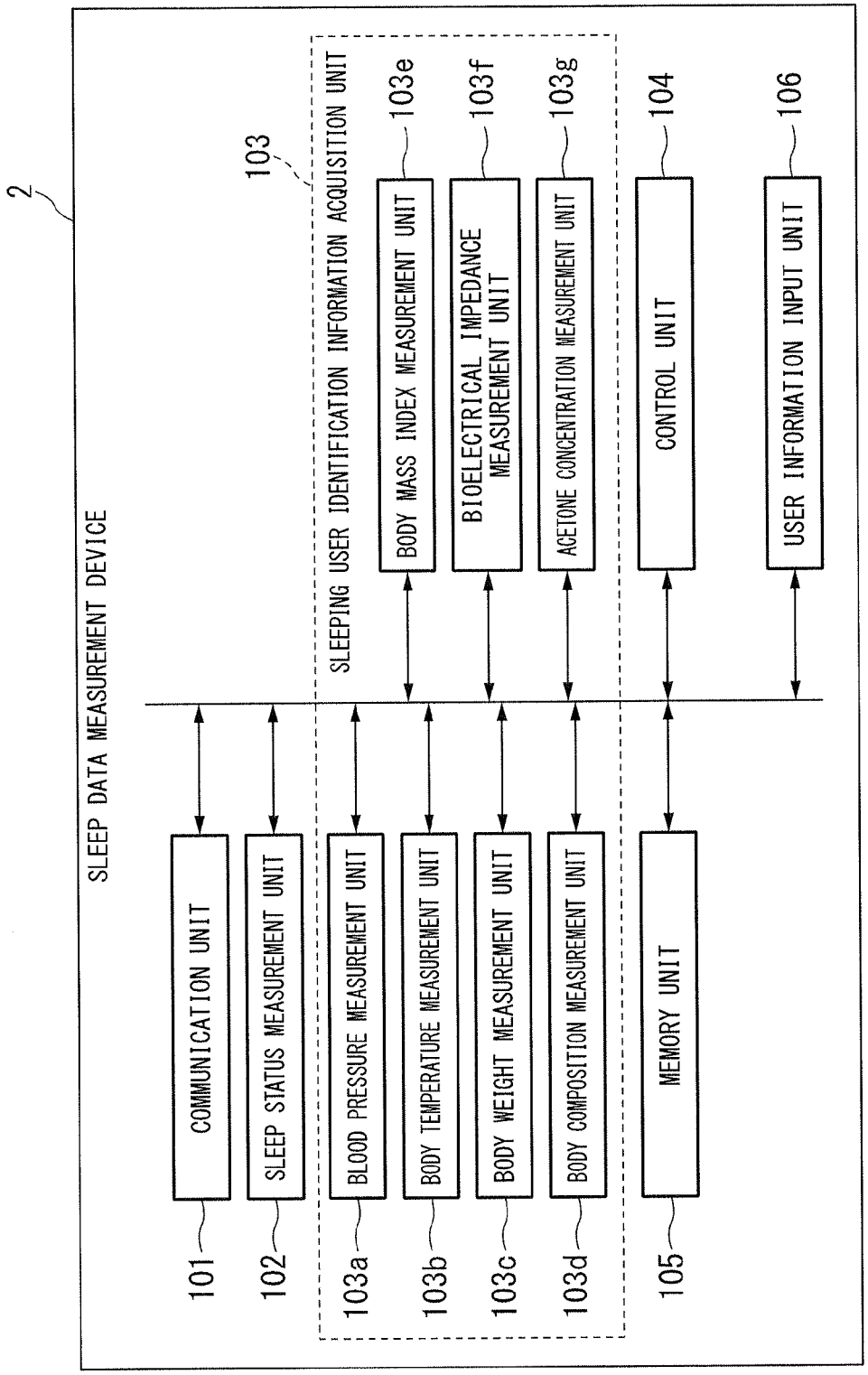
FIG. 2 is a diagram showing an example of a configuration of a sleep data measurement device according to the present embodiment.

FIG. 2 is a diagram showing an example of the configuration of the sleep data measurement device according to the present embodiment.

The sleep data measurement device 2 includes a communication unit 101, a sleep status measurement unit 102, a sleeping user identification information acquisition unit 103 configured to acquire measurement information of a body of the user as sleeping user identification information for identifying the user, a control unit 104, a memory unit 105 and a user information input unit 106.

The communication unit 101 included in the sleep data measurement device 2 communicates with the server 4 via the network NW.

The sleep status measurement unit 102 measures the sleep data of the user such as pulse, respiration or body motion etc. during sleep.

When the sleep status measurement unit 102 measures the sleep data of the user, the sleeping user identification information acquisition unit 103 acquires measurement information of a body of the user as sleeping user identification information for identifying the user. In addition, the sleeping user identification information acquisition unit 103 may acquire any measurement information of the body of the user as far as the information enables to identify the user adequately.

The sleeping user identification information acquisition unit 103 acquires the sleeping user identification information as follows, for example. The sleeping user identification information acquisition unit 103 includes a blood pressure measurement unit 103a, a body temperature measurement unit 103b, a body weight measurement unit 103c, a body composition measurement unit 103d, a body mass index measurement unit 103e, a bioelectrical impedance measurement unit 103f and an acetone concentration measurement unit 103g.

When the sleep status measurement unit 102 measures the sleep data of the user, the blood pressure measurement unit 103a measures the blood pressure of the user. For example, the blood pressure measurement unit 103a is an automatic blood pressure gauge including a microphone in the position corresponding to a blood vessel of the user, to measure the blood pressure by reading in sound changes of the blood vessel.

When the sleep status measurement unit 102 measures the sleep data of the user, the body temperature measurement unit 103b measures the body temperature of the user. For example, the body temperature measurement unit 103b is a temperature gauge using an ear thermometer, an infrared thermometer or platinum resistance temperature detector or the like.

When the sleep status measurement unit 102 measures the sleep data of the user, the body weight measurement unit 103c measures the body weight of the user. For example, the body weight measurement unit 103c is a body weight gauge which calculates the body weight based on the load detected by the load sensor (for example, a load cell) included in the measurement stand.

The body composition measurement unit 103d conducts measurement by calculating the body composition based on bioelectrical impedance of the user measured by a bioelectrical impedance measurement unit 103f, the body weight of the user measured by the body weight measurement unit 103c and user information input by the user information input unit 106. For example, the body composition measurement unit 103d measures muscle, body fat and the like by bioelectrical impedance analysis. At this time, the body composition measurement unit 103d measures the body composition with high precision by using multiple frequency measurement, reactance technology or the like.

In addition, multiple frequency measurement is a measurement based on a characteristic of current which flows in different routes depending on the frequency in biological tissue. The multiple frequency measurement is to obtain detailed information of cells in biological tissue by using currents of multiple frequencies separately. Reactance technology is a technology where biological tissue is represented in an electrical equivalent circuit assuming intracellular fluid and extracellular fluid to be a resistance component, and a cell membrane to be capacitance component. The reactance technology is a technology to obtain information of intercellular fluid and extracellular fluid as well as information of cell membrane by measuring the resistance and the capacitance.

The body mass index measurement unit 103e calculates the body mass index of the user based on the body weight and height of the user. The body mass index is an index called BMI (Body Mass Index), which is a criterion to determine degree of obesity through balance of body weight and height. For example, the body mass index measurement unit 103e calculates "Body Weight (kg)÷Height (m)÷Height (m)" using the height which the user input through the user information input unit 106 into the sleep data measurement device 2 and the body weight measured by the body weight measurement unit 103c.

The bioelectrical impedance measurement unit 103f measures bioelectrical impedance of the user. For example, the bioelectrical impedance measurement unit 103f includes two current supplying electrodes and two voltage measuring electrodes. The bioelectrical impedance measurement unit 103f conducts measurement by applying a faint alternate current through the body of the user through two current supplying electrodes, and detecting the voltage (electrical potential difference) through two voltage measuring electrodes, and finding the bioelectrical impedance of the user based on the detection results.

The acetone concentration measurement unit 103g measures the concentration of acetone contained in the exhaled gas of the user. For example, the acetone concentration measurement unit 103g detects gas containing acetone in exhaled gas using the first gas sensor and detects gas other than acetone in the exhaled gas using the second gas sensor. The acetone concentration measurement unit 103g measures by finding the acetone concentration based on the difference between gas components detected.

In addition, the sleeping user identification information acquisition unit 103 is not limited to those including all of the blood pressure measurement unit 103a, the body temperature measurement unit 103b, the body weight measurement unit 103c, the body composition measurement unit 103d, the body mass index measurement unit 103e, the bioelectrical impedance measurement unit 103f, and the acetone concentration measurement unit 103g. The sleeping user identification information acquisition unit 103 including at least one among the blood pressure measurement unit 103a, the body temperature measurement unit 103b, the body weight measurement unit 103c, the body composition measurement unit 103d, the body mass index measurement unit 103e, the bioelectrical impedance measurement unit 103f, and the acetone concentration measurement unit 103g, is capable of acquiring the sleeping user identification information, and preferably including more than one.

The control unit 104 conducts various controls in the sleep data measurement device 2. For example, the control unit 104 controls communication conducted by the communication unit 101.

The memory unit 105 stores various data needed for a process in the sleep data measurement device 2. For example, the memory unit 105 stores the sleeping user identification information acquired by the sleeping user identification information acquisition unit 103.

The user information input unit 106 acquires information used to identify the user, based on the operation by the user at the time of initial registration for the first time use of the sleep data measurement device 2. For example, the user information input unit 106 acquires information such as name, age and the like, which are input based on the operation by the user at the time of initial registration for the first time use of the sleep data measurement device 2. Also, for example, the user information input unit 106 acquires sex information used to enhance the precision of identification of the user by blood pressure, based on the operation by the user at the time of initial registration for the first time use of the sleep data measurement device 2. Also, for example, the user information input unit 106 acquires height information used when calculating the body mass index. The user information input unit 106 is, for example, a touch panel, keyboard, or the like.

Next, a configuration of the vehicle 3 according to the present embodiment will be described.

Figure 3:
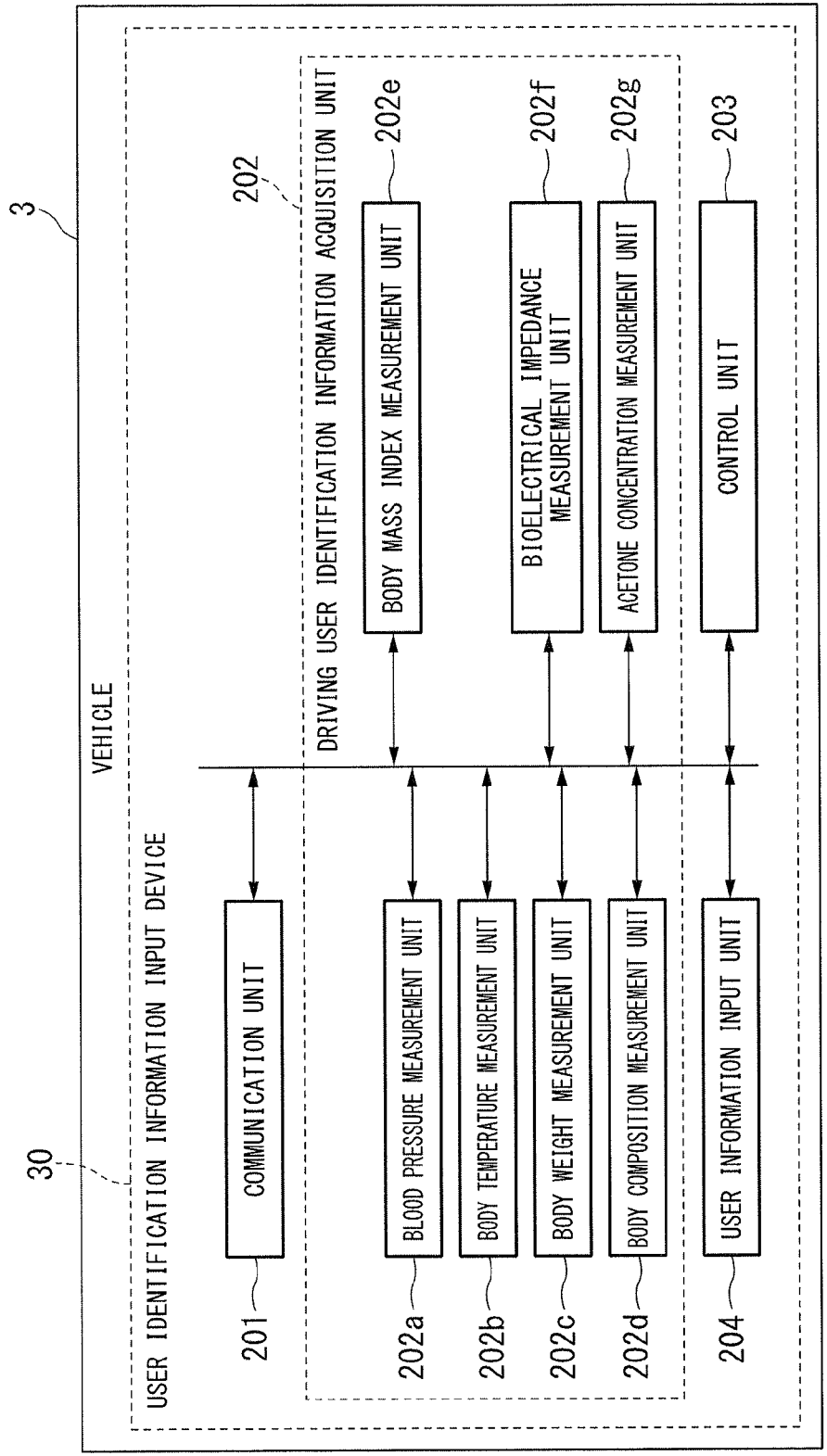
FIG. 3 is a diagram showing an example of a configuration of a vehicle according to the present embodiment.

FIG. 3 is a diagram showing an example of the configuration of the vehicle 3 according to the present embodiment.

The vehicle 3 included in the safe driving management system 1 includes the user identification information input device 30.

The user identification information input device 30 includes a communication unit 201, a driving user identification information acquisition unit 202 configured to acquire measurement information of a body of the user as driving user identification information for identifying the user, a control unit 203, and a user information input unit 204.

The communication unit 201 included in the vehicle 3 communicates with the server 4 via the network NW.

When the user drives the vehicle 3, the driving user identification information acquisition unit 202 acquires measurement information of a body of the user as driving user identification information for identifying the user. In addition, the driving user identification information acquisition unit 202 may be anything as far as acquiring the same sort of user identification information as the sleeping user identification information acquisition unit 103 acquires.

The driving user identification information acquisition unit 202 acquires the driving user identification information as follows, for example. The driving user identification information acquisition unit 202 includes a blood pressure measurement unit 202a, a body temperature measurement unit 202b, a body weight measurement unit 202c, a body composition measurement unit 202d, a body mass index measurement unit 202e, a bioelectrical impedance measurement unit 202f and an acetone concentration measurement unit 202g.

When the user drives the vehicle 3, the blood pressure measurement unit 202a measures the blood pressure of the user. For example, the blood pressure measurement unit 202a is an automatic blood pressure gauge including a microphone in the position corresponding to a blood vessel of the user, to measure the blood pressure by reading sound changes of the blood vessel.

When the user drives the vehicle 3, the body temperature measurement unit 202b measures the body temperature of the user. For example, the body temperature measurement unit 202b is a temperature gauge using an ear thermometer, an infrared thermometer or platinum resistance temperature detector etc.

When the user drives the vehicle 3, the body weight measurement unit 202c measures the body weight of the user. For example, the body weight measurement unit 202c is a body weight gauge which calculates the user's body weight based on the load detected by the load sensor (for example, a load cell) included in the measurement stand. In addition, in a case where a part of the body weight of the driver is applied on the floor as the feet of the driver reach the floor, and total body weight of the driver is not applied on the seating face of the seat, the body weight measurement unit 202c estimates the total body weight of the user based on the correlation between the load detected by the load sensor, found by experiments, or the like in advance and the total body weight of the driver.

The body composition measurement unit 202d conducts measurement by calculating the body composition based on bioelectrical impedance of the user measured by a bioelectrical impedance measurement unit 202f, the body weight of the user measured by the body weight measurement unit 202c and user information input by the user information input unit 204. For example, the body composition measurement unit 202d measures muscle, body fat and the like by bioelectrical impedance analysis. At this time, the body composition measurement unit 202d measures the body composition with high precision by using multiple frequency measurement or reactance technology and the like.

The body mass index measurement unit 202e calculates the body mass index of the user based on the body weight and height of the user. For example, the body mass index measurement unit 202e calculates "Body Weight (kg) ÷Height (m)÷Height (m)" using the height which the user input through the user information input unit 204 into the vehicle 3 and the body weight measured by the body weight measurement unit 202c.

The bioelectrical impedance measurement unit 202f measures bioelectrical impedance of the user. For example, the bioelectrical impedance measurement unit 202f includes two current supplying electrodes and two voltage measuring electrodes at the steering wheel. The bioelectrical impedance measurement unit 202f measures the bioelectrical impedance by applying faint alternate current in the body of the user when the user grab the steering wheel through two current supplying electrodes, and by detecting the voltage (electrical potential difference) through two voltage measuring electrodes, based on which the bioelectrical impedance of the user is found.

The acetone concentration measurement unit 202g measures the concentration of acetone contained in the exhaled gas of the user. For example, the acetone concentration measurement unit 202g detects gas containing acetone component in the exhaled gas by the first gas sensor and detects gas component other than acetone component in the exhaled gas by the second gas sensor. The acetone concentration measurement unit 202g conducts measurement by finding the acetone concentration based on the difference between gas components detected.

In addition, the driving user identification information acquisition unit 202 is not limited to the unit including the blood pressure measurement unit 202a, the body temperature measurement unit 202b, the body weight measurement unit 202c, the body composition measurement unit 202d, the body mass index measurement unit 202e, the bioelectrical impedance measurement unit 202f and the acetone concentration measurement unit 202g. The driving user identification information acquisition unit 202 including at least one among the blood pressure measurement unit 202a, the body temperature measurement unit 202b, the body weight measurement unit 202c, the body composition measurement unit 202d, the body mass index measurement unit 202e, the bioelectrical impedance measurement unit 202f and the acetone concentration measurement unit 202g, is capable of acquiring the driving user identification information, and preferably including more than one.

The control unit 203 conducts various controls of the vehicle 3. For example, the control unit 203 controls communication conducted by the communication unit 201. Also, the control unit 203 controls whether or not to allow the user drive based on the determination result received from the server 4 of whether the user is in sleep shortage or not.

The user information input unit 204 acquires information used to identify the user, based on the operation by the user at the time of initial registration for the first time use of the user identification information input device 30. For example, the user information input unit 204 acquires information such as name, age, and the like, which are input based on the operation by the user at the time of initial registration for the first time use of the user identification information input device 30. Also, for example, the user information input unit 204 acquires sex information used to enhance the precision of identification of the user by blood pressure, based on the operation by the user at the time of initial registration for the first time use of the user identification information input device 30. Also for example, the user information input unit 204 acquires height information used when calculating the body mass index. The user information input unit 204 is, for example, a touch panel, keyboard, or the like.

Next, a configuration of the server 4 according to the present embodiment will be described.

Figure 4:
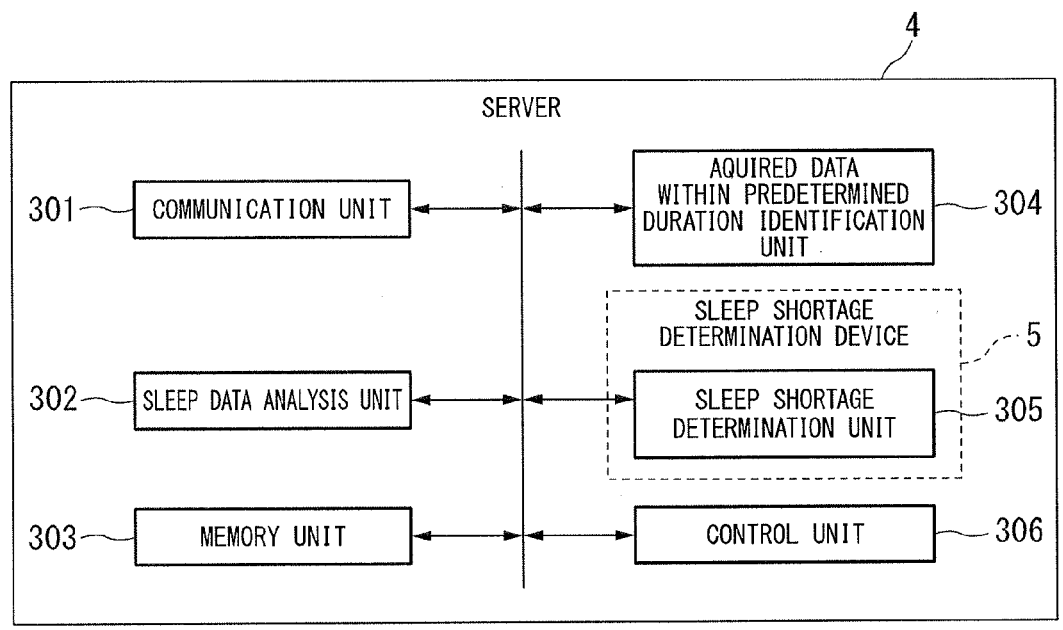
FIG. 4 is a diagram showing an example of a configuration of a server according to the present embodiment.

FIG. 4 is a diagram showing an example of the configuration of the server 4 according to the present embodiment.

The server 4 included in the safe driving management system 1 includes a communication unit 301, a sleep data analysis unit 302, a memory unit 303, an acquired data within predetermined duration identification unit 304 configured to identify sleep data within predetermined duration as acquired data within predetermined duration, a sleep shortage determination device 5, and a control unit 306. In addition, the sleep shortage determination device 5 includes a sleep shortage determination unit 305.

The communication unit 301 included in the server 4 communicates with the sleep data measurement device 2 and the vehicle 3 via the network NW.

The sleep data analysis unit 302 acquires the sleep data of the user from the sleep status measurement unit 102 and the sleeping user identification information from the sleeping user identification information acquisition unit 103 via the communication unit 301. And the sleep data analysis unit 302 compares the sufficient sleep data with the determination flag and acquired sufficient sleep data, and determines whether the user's sleep is sufficient or not.

Every time upon receiving the sleep data of the user and the sleeping user identification information via the network NW from the sleep data measurement device 2, the sleep data analysis unit 302 analyzes whether the user's sleep is sufficient or not, and stores the aforementioned determination result associated with the sleep data of the user and the sleeping user identification information in the memory unit 303. More specifically, in a case where the determination result was that sleep is sufficient, the sleep data analysis unit 302 stores the sleep data and the sleeping user identification information of the user associated with the sufficient sleep flag as the sufficient sleep data in the memory unit 303.

The memory unit 303 stores various information needed for a process of the server 4. The memory unit 303, for example, stores the sleep data of the user and the sleeping user identification information associated with the determination result of whether the user's sleep is sufficient or not by the sleep data analysis unit 302. In a case where the sleep data analysis unit 302 determines that the user's sleep is sufficient, the memory unit 303 stores the sleep data and the sleep user identification information together with the sufficient sleep flag indicating that the user's sleep is sufficient.

When the user drives the vehicle 3, the acquired data within predetermined duration identification unit 304 compares each of the driving user identification information measured by the vehicle 3 and the sleeping user identification information in the data table stored in the memory unit 303 respectively. For example, when the user drives the vehicle 3, the acquired data within predetermined duration identification unit 304 compares blood pressure contained in the driving user identification information acquired by the driving user identification information acquisition unit 202 and the blood pressure contained in the sleeping user identification information stored by each user in the data table stored in the memory unit 303.

Also, the acquired data within predetermined duration identification unit 304 identifies the sleeping user identification information which is identical to the driving user identification information. For example, the acquired data within predetermined duration identification unit 304 compares blood pressure contained in the driving user identification information and blood pressure contained in each of the sleeping user identification information stored in a memory unit 303 in orderly manner, and identifies the sleeping user identification information containing the blood pressure which is the nearest value to the blood pressure contained in the driving user identification information. That is, the data table identified by the acquired data within predetermined duration identification unit 304 containing the sleeping user identification information is identified as the data table corresponding to the user boarded the vehicle 3.

The acquired data within predetermined duration identification unit 304 identifies the sleep data within predetermined duration in the past, among stored sleep data associated with identified sleeping user identification information. For example, among stored sleep data associated with the sleeping user identification information, the acquired data within predetermined duration identification unit 304 identifies the sleep data within 24 hours from present in the past, and identifies the identified sleep data as the acquired data within predetermined duration.

The sleep shortage determination unit 305 determines whether the user's sleep is sufficient for driving the vehicle 3 or not when the user drives based on the acquired data within predetermined duration in the identified data table. For example, in a case where the total of the sleep time in the sleep data with sufficient sleep flag in the acquired data within predetermined duration is 8 hours or more, the server 4 (the sleep shortage determination unit 305) determines that the user's sleep is sufficient for driving vehicle 3. Also, in a case where the total of the sleep time in the sleep data with sufficient sleep flag in the acquired data within predetermined duration is less than 8 hours, the server 4 (the sleep shortage determination unit 305) determines that the user's sleep is insufficient for driving vehicle 3.

Also, the sleep shortage determination unit 305 transmits the determination result of whether the user's sleep is sufficient for driving vehicle 3 or not to the vehicle 3.

The control unit 306 conducts various controls of the server 4. For example, the control unit 306 controls communication conducted by the communication unit 301.

Next, data stored in the memory unit 303 included in the server 4 according to the present embodiment will be described.

FIG. 5 is a diagram showing an example of data stored by the memory unit 303 included in the server 4 according to the present embodiment.

The memory unit 303 associates the sleeping user identification information of the user measured by each sleep on the mattress of bedding such as blood pressure, body temperature, body weight, body composition (body fat, visceral fat, subcutaneous fat, muscle, bone, body water and other components within body), body mass index, bioelectrical impedance, acetone concentration in exhaled gas with the sleep data such as time, respiration, pulse or the like, and stores as shown in the data table TBL1 in FIG. 5.

The memory unit 303 associates an initial sleep data in which the user's sleep is sufficient for driving the vehicle 3 with the sleeping user identification information. Then memory unit 303 then stores the initial sleep data and the sleeping user identification information in a data table together with a sufficient sleep flag indicating sufficient sleep data and a determination flag indicating that the initial sleep data and the sleeping user identification information are used as determination criteria when analyzing the sleep state. In case of the data table TBL 1 shown in FIG. 5, data 1 is the initial sleep data where the user's sleep is sufficient for driving vehicle 3. The memory unit 303 associates the sleep data and the sleeping user identification information, and stores together with the sufficient sleep flag "1" indicating the sufficient sleep data and the determination flag "1" indicating that data 1 is used for determination criteria when sleep status is analyzed, in the data table TBL 1.

Every time upon receiving the sleep data of the user and the sleeping user identification information via the network NW, the sleep data analysis unit 302 in the server 4 compares the sufficient sleep data stored together with the determination flag and the sleep data of the user which the sleep data measurement device 2 measured, and analyze the sleep status of the user which the sleep data measurement device 2 measured. For example, the sleep data analysis unit 302 compares the number of respirations per unit of time, the number of pulses per unit of time and the strength of pulse contained in the sleep sufficient data of data 1 stored together with the determination flag "1" and the sufficient sleep flag "1" in the data table TBL1 shown in FIG. 5 and a number of respirations per unit of time, a number of pulses per unit of time and strength of pulse contained in sleep data of each sleep of the user respectively. Then, in a case where the sleep data analysis unit 302 determines the number of respirations per unit of time, the number of pulses per unit of time and the strength of pulse contained in the sleep data of data 1 and the number of respirations per unit of time, the number of pulses per unit of time and strength of pulse contained in the sleep data of each sleep of the user are identical respectively, the sleep data analysis unit 302 determines that the user's sleep is sufficient. More specifically, the sleep data analysis unit 302 subtracts the number of respirations per unit of time contained in the sleep data of each sleep of the user from the number of respirations per unit of time contained in the sleep data of data 1 stored together with the determine flag "1" and the sufficient sleep flag "1". The sleep data analysis unit 302 compares a number of respirations subtraction result which is a subtraction result of the aforementioned number of respirations, to a number of respirations threshold value which is preset to determine that the number of respirations per unit of time contained in the sleep data of data 1 and the number of respirations per unit of time contained in the sleep data of each sleep of the user are identical. In case the number of respirations subtraction result is smaller than the number of respirations threshold value, the sleep data analysis unit 302 determines that the number of respirations per unit of time contained in the sleep data is identical to the number of respirations per unit of time contained in the sleep data of data 1. The sleep data analysis unit 302 compares a number of pulses subtraction result which is a subtraction result of the aforementioned number of pulses, to a number of pulses threshold value which is preset to determine that the number of pulses per unit of time contained in the sleep data of data 1 and the number of pulses per unit of time contained in the sleep data of each sleep of the user are identical. In case the number of pulses subtraction result is smaller than the number of pulses threshold value, the sleep data analysis unit 302 determines that the number of pulses per unit of time contained in the sleep data is identical to the number of pulses per unit of time contained in the sleep data of data 1. The sleep data analysis unit 302 compares a strength of pulse subtraction result which is a subtraction result of the aforementioned strength of pulse, to strength of pulse threshold value which is preset to determine that the strength of pulse contained in the sleep data of data 1 and the strength of pulse contained in the sleep data of the user's each sleep are identical. In case the strength of pulse subtraction result is smaller than the strength of pulse threshold value, the sleep data analysis unit 302 determines that the strength of pulse contained in the sleep data is identical to the strength of pulse contained in the sleep data of data 1. Thereafter, in case where the sleep data analysis unit 302 determines all of the number of respirations per unit of time, the number of pulses per unit of time and the strength of pulse contained in the sleep data of data 1 and the number of respirations per unit of time, the number of pulses per unit of time and strength of pulse contained in the sleep data of each sleep of the user are identical respectively, the sleep data analysis unit 302 determines that the user's sleep is sufficient.

The sleep data analysis unit 302 stores the sleeping user identification information corresponding to the sleep data of the user in which the user's sleep is determined to be sufficient, together with the sufficient sleep flag in the data table TBL1 corresponding to the user in the memory unit 303. For example, the sleep data analysis unit 302 stores the sleeping user identification information corresponding to the sleep data of the user in which the user's sleep is determined to be sufficient, like data 3 and data 4 in the data table TBL1 shown in FIG. 5, together with the sufficient sleep flag "1" in the data table TBL 1 corresponding to the user in the memory unit 303.

Also, in case the data analysis unit 302 determines any of the number of respirations per unit of time, the number of pulses per unit of time and the strength of pulse contained in the sleep data of the data 1 and the number of respirations per unit of time, the number of pulses per unit of time and strength of pulse contained in the sleep data of the user's each sleep are not identical to each other, the sleep data analysis unit 302 determines that the user's sleep is not sufficient.

In addition, the sleep data analysis unit 302 may take the latest sleep data stored with the sufficient sleep flag "1" in the memory unit 303 as the sleep data to use as the determination criteria when analyzing the sleep status. For example, in a case where the times in the data table TBL1 shown in FIG. 5 are in chronological order like time data 1, 2, 3 . . . , the sleep data analysis unit 302 may take the sleep data of the data 4 as the sleep data to use as the determination criteria when analyzing the sleep status, and store the sleep data of the data 4 together with the determination flag "1" in the memory unit 303.

Next, how measurement information of a body of a user can be user identification information will be described taking an example of the blood pressure (including pulse wave at that time) by using FIG. 6 and FIG. 7.

Figure 6:
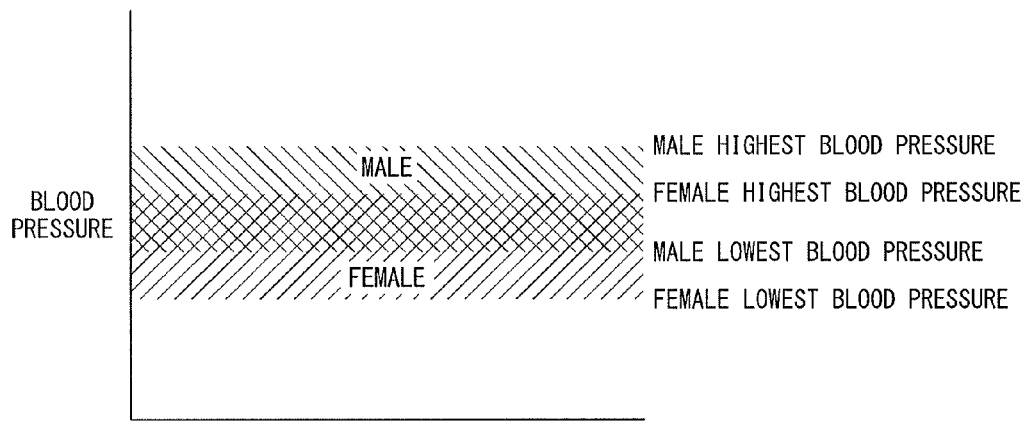
FIG. 6 is a diagram showing an example of a difference of the blood pressure between female and male according to the present embodiment.

FIG. 6 is a diagram showing an example of a difference of blood pressure between female and male according to the present embodiment.

In FIG. 6, the vertical axis indicates blood pressure.

Ordinarily, blood pressure of an identical person varies according to activity status within one day. However, in case where the blood pressure is measured in the regular and stable conditions within one day, variation of the blood pressure by every day is not so large. FIG. 6 indicates the highest blood pressure and the lowest blood pressure measured under stable conditions.

As shown in FIG. 6, there is a difference between the range from the highest blood pressure to the lowest blood pressure of a female and the range from the highest blood pressure to the lowest blood pressure of a male. The range from the highest blood pressure to the lowest blood pressure of a female indicates a tendency that is relatively low with respect to the range from the highest blood pressure to the lowest blood pressure of a male.

Accordingly, in case where the blood pressure between the highest blood pressure of female and the highest blood pressure of male is indicated, there is a higher possibility that the person is a male. Therefore, the blood pressure can be user identification information.

Figure 7:
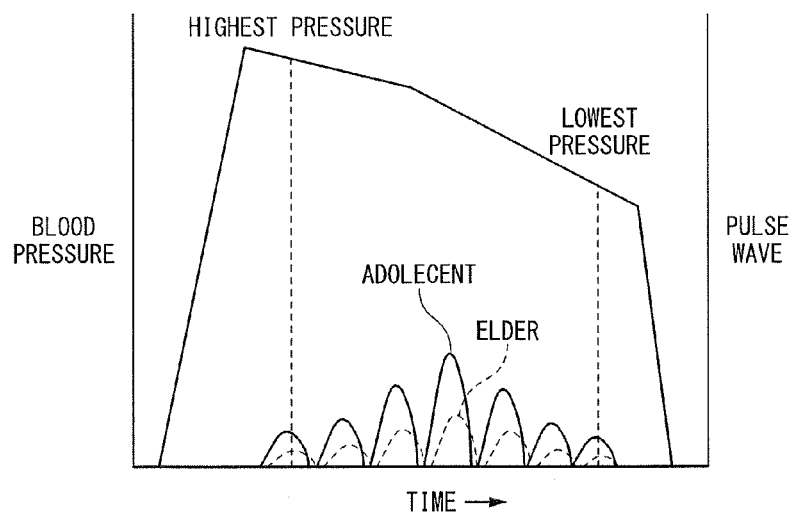
FIG. 7 is a diagram showing an example of a difference of the blood pressure between elder and adolescent according to the present embodiment.

FIG. 7 is a diagram showing an example of a difference of the blood pressure between elder and adolescent according to the present embodiment.

In FIG. 7, the horizontal axis indicates time, and the vertical axis indicates blood pressure and pulse wave.

FIG. 7 shows raw data of the pulse wave between measurements of the highest blood pressure and the lowest blood pressure as well as measured values of the highest blood pressure and the lowest blood pressure.

As shown in FIG. 7, the peak value of the raw data of pulse wave of an elder indicates a tendency that is relatively low with respect to a peak value of the raw data of pulse wave of adolescent.

Accordingly, the threshold value is preset between the peak value of the raw data of the pulse wave of an elder and the peak value of the raw data of pulse wave of an adolescent. And in a case where the peak value of the raw data of pulse wave is lower than the threshold value, the person is determined to be an elder, while in a case where the peak value of the raw data of pulse wave is higher than the threshold value, the person is determined to be an adolescent, by which it is possible to determine between an elder and an adolescent. Therefore, the blood pressure and the pulse wave can be user identification information.

Accordingly, by using such information measured by a blood pressure gauge as the highest blood pressure, the lowest blood pressure, the peak value of the raw data of pulse wave, an area of the raw data of pulse wave and the like, it is possible to enhance the precision of user identification.

Next, a process of the safe driving management system 1 according to the present embodiment will be described.

Figure 8:
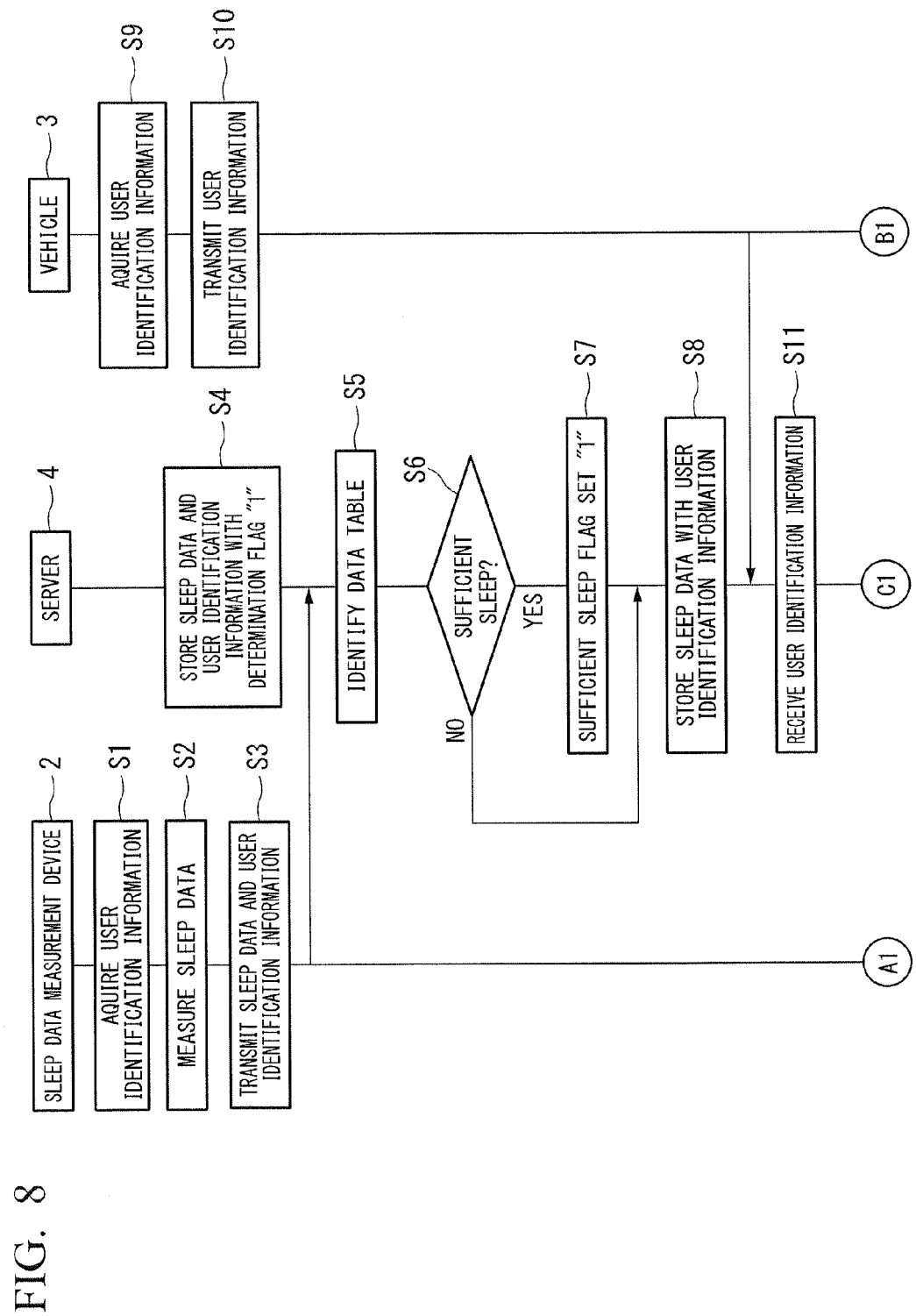
FIG. 8 is a diagram showing an example of a process flow of the safe driving management system according to the present embodiment.
Figure 9:
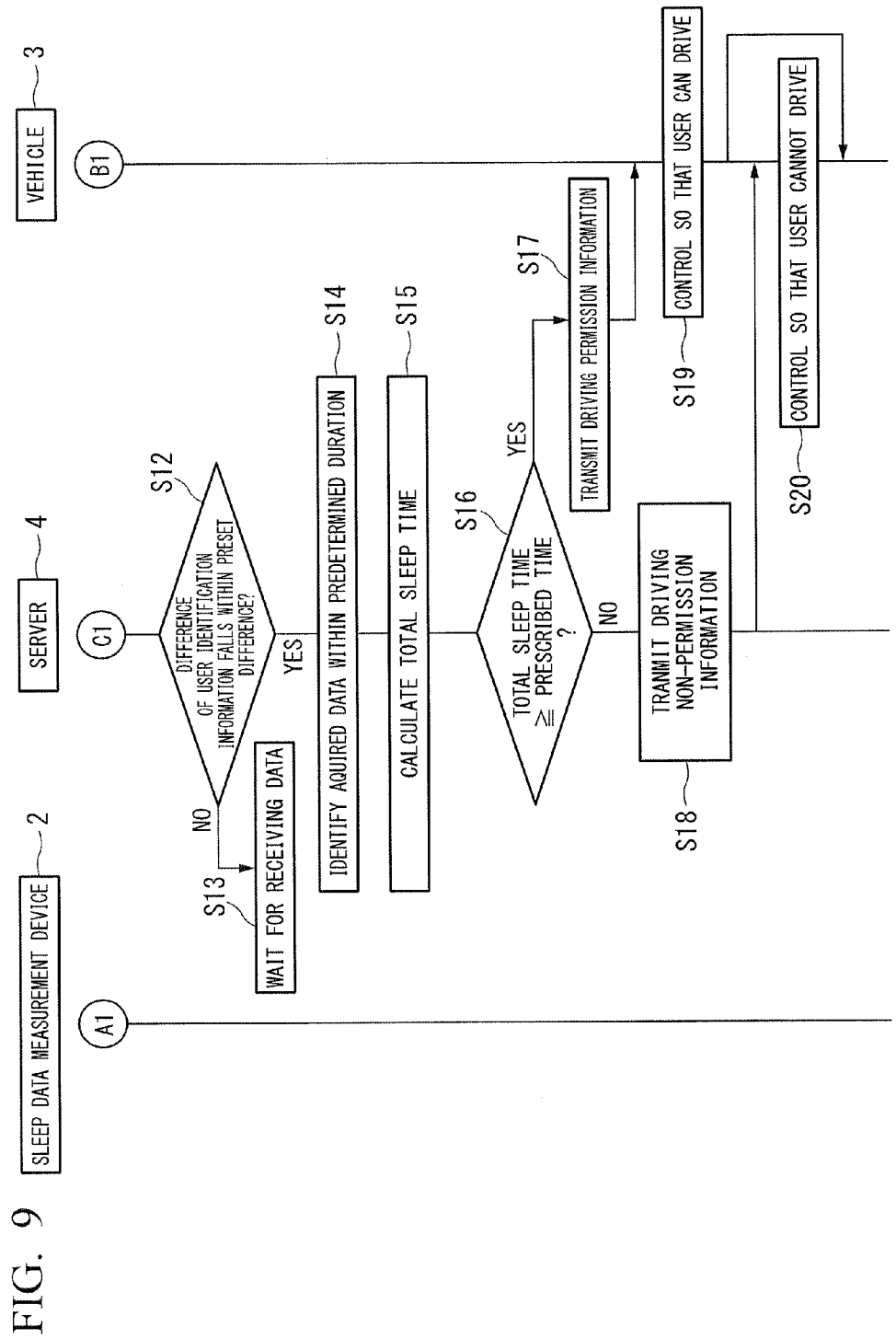
FIG. 9 is a diagram showing an example of a process flow of the safe driving management system according to the present embodiment.

FIG. 8 and FIG. 9 are diagrams showing an example of the process flow of the safe driving management system according to the present embodiment.

In addition, in the safe driving management system 1, the sleep data measurement device 2, vehicle 3, and server 4 actually conduct communication via the network NW, but in the process flow shown in FIG. 8 and FIG. 9, the network NW is omitted. Also, regarding the communication conducted by the sleep data measurement device 2, vehicle 3 and the server 4, each control unit actually controls the communication. But in following description, the control unit is assumed to conduct control of communication, and the description of control itself is omitted.

First, a process in which the sleep data measurement device 2 measures the sleep data of the user when the user sleeps will be described.

The user makes such preparations for the sleep data measurement device 2 to measure the sleep data during sleep as wearing a device having a function of the sleeping user identification information acquisition unit 103, or getting on a mattress of bedding having a function of the sleeping user identification information acquisition unit 103. In addition, the user inputs information used to identify the user into the user information input unit 106, based on the operation by the user at the time of initial registration for the first time use of the sleep data measurement device 2. For example, the user inputs such information as name, age, or the like to the user information input unit 106 based on the operation by the user at the time of initial registration for the first time use of the sleep data measurement device 2. Also, for example, the user input information of sex used to enhance the precision of the user identification by the blood pressure to the user information input unit 106 based on the operation by the user at the time of initial registration for the first time use of the sleep data measurement device 2. Also, for example, the user input information of the body used to calculate the body mass index to the user information input unit 106 based on the operation by the user at the time of initial registration for the first time use of the sleep data measurement device 2.

Once the user completes the initial registration for the first time use of the sleep data measurement device 2, the sleeping user identification information acquisition unit 103 included in the sleep data measurement device 2 acquires the sleeping user identification information when the sleep status measurement unit 102 is to measure the sleep data of the user (Step S1). For example, right before the sleep status measurement unit 102 measures the sleep data of the user, the blood pressure measurement unit 103a measures the blood pressure, which is one of body characteristics of the user, as the sleeping user identification information. Also, for example, when the sleep status measurement unit 102 measures the sleep data of the user, the body temperature measurement unit 103b, measures the body temperature of the user. Also, for example, the body weight measurement unit 103c measures the body weight of the user, which is one of body characteristics of the user, as the sleeping user identification information. Also, for example, the body composition measurement unit 103d measures body composition, which is one of body characteristics of the user, as the sleeping user identification information based on the bioelectrical impedance of the user measured by the bioelectrical impedance measurement unit 103f, the body weight of the user measured by the body weight measurement unit 103c and the user information input by the user information input unit 106. Also, for example, the body mass index measurement unit 103e calculates the body mass index of the user, which is one of body characteristics of the user, as the sleeping user identification information based on the body weight and the height of the user. Also, for example, the acetone concentration measurement unit 103g measures the acetone concentration contained in the exhaled gas of the user, which is one of body characteristics of the user, as the sleeping user identification information.

The sleeping user identification information acquisition unit 103 stores acquired sleeping user identification information in the memory unit 105.

Upon acquiring the sleeping user identification information, the sleeping user identification information acquisition unit 103 outputs a signal indicating that the acquisition of the sleeping user identification information is completed (hereinafter "sleeping user identification information acquisition completed signal"), to the sleep status measurement unit 102.

In addition, the sleeping user identification information acquisition unit 103 may use finger print, voice print, or the like of the user, which is one of body characteristics of the user, as the sleeping user identification information.

Upon the sleeping user identification information acquisition completed signal being input from the sleeping user identification information acquisition unit 103, the sleep status measurement unit 102 measures the sleep data such data as pulse, respiration, body motion, or the like of the user during sleep (Step S2).

The sleep status measurement unit 102 reads out the sleeping user identification information, which the sleeping user identification information acquisition unit 103 stored in the memory unit 105, from the memory unit 105. In addition, the sleep status measurement unit 102 transmits the sleep data of the user measured and the sleeping user identification information read out, via the communication unit 101 to the server 4 (Step S3). In addition, in a case where there is the registration of the user information by the user, the sleep status measurement unit 102 transmits the user information together with the sleep data and the sleeping user identification information to the server 4. Also, a data table TBL1 like the one shown in FIG. 5 is generated in the server 4 with respect to the user indicated by the user information.

In addition, it is possible to imagine a case where a user at the time when the sleeping user identification information acquisition unit 103 acquires the sleeping user identification information and a user at the time when the sleep status measurement unit 102 measures the sleep data are different. Therefore, the sleeping user identification information acquisition unit 103 preferably acquires the sleeping user identification information in parallel during the sleep status measurement unit 102 measures the sleep data. For example, the sleeping user identification information acquisition unit 103 acquires the sleeping user identification information in a state in which the user is on the mattress of bedding with a function of the body weight gauge. And, while the sleeping user identification information acquisition unit 103 detecting that the body weight of the user on the mattress does not change, the sleep status measurement unit 102 acquires the sleep data in that state. In a case where the sleeping user identification information acquisition unit 103 detects the change of the body weight of the user on the mattress, the sleeping user identification information acquisition unit 103 determines that the users are different, and the sleep status measurement unit 102 suspends the acquisition of the sleep data. In this way, it is possible to measure the sleep data of the identical user.

Next, a process in which the server 4 associates the sleep data and the sleeping user identification information, and stores information on each user will be described.

The sleep data analysis unit 302 included in the server 4 associates an initial sleep data in which the user's sleep is sufficient for driving the vehicle 3 with the sleeping user identification information. Then, the sleep data analysis unit 302 stores the initial sleep data and the sleeping user identification information in a data table of each user TBL 1 together with a sufficient sleep flag "1" indicating sufficient sleep data and a determination flag "1" indicating that the initial sleep data and the sleeping user identification information are used as determination criteria when analyzing the sleep state (Step S4).

Every time the sleep data analysis unit 302 included in the server 4 receives the sleep data and the sleeping user identification information of the user from the sleep data measurement device 2 via the network NW, the sleep data analysis unit 302 in the server 4 compares the sleeping user identification information received and the sleeping user identification information in the data table TBL 1 of each user. And the sleep data analysis unit 302 identifies data table TBL1 with the sleeping user identification information identical to the sleeping user identification information received (Step S5). For example, in case where the sleeping user identification information received is blood pressure, the sleep data analysis unit 302 compares the blood pressure received and blood pressure of data with the determination flag "1" in data table TBL 1 corresponding to each user. And in a case where the difference between the blood pressure received and the blood pressure of the data with the determination flag "1" in the data table TBL 1 corresponding to each user falls within the preset difference, the sleep data analysis unit 302 identifies the data table TBL 1 of the user corresponding to the sleeping user identification information received.

Also, the sleep data analysis unit 302 compares the sufficient sleep data stored together with the determination flag "1" in the data table TBL 1 identified and the sleep data of the user received from the sleep data measurement device 2, and determines whether the user's sleep measured by the sleep data measurement device 2 is sufficient or not (Step S6). For example, the sleep data analysis unit 302 compares the number of respirations per unit of time, the number of pulses per unit of time and the strength of pulse contained in the sleep sufficient data of data 1 stored together with the determination flag "1" and the sufficient sleep flag "1" in the data table TBL1 shown in FIG. 5 and the number of respirations per unit of time, the number of pulses per unit of time and strength of pulse contained in sleep data of each sleep of the user respectively. Then, in a case where the sleep data analysis unit 302 determines the number of respirations per unit of time, the number of pulses per unit of time and the strength of pulse contained in the sleep data of data 1 and the number of respirations per unit of time, the number of pulses per unit of time and strength of pulse contained in the sleep data of each sleep of the user are identical respectively, the sleep data analysis unit 302 determines that the user's sleep is sufficient (Step S6, YES). In this case, the sleep data analysis unit 302 sets the sufficient sleep flag "1" (Step S7), and stores the sleep data together with the sleeping user identification information in the memory unit 303 (Step S8).

Also, in a case the data analysis unit 302 determines any of the number of respirations per unit of time, the number of pulses per unit of time and the strength of pulse contained in the sleep data of the data 1 and the number of respirations per unit of time, the number of pulses per unit of time and strength of pulse contained in the sleep data of each sleep of the user is not identical to each other, determines in the process of Step S6 that the user's sleep is not sufficient (Step S6, NO). In this case, the sleep data analysis unit 302 stores the sleep data together with the sleeping user identification information in the memory unit 303 without conducting the process of Step S7 (Step S8).

In this way, the memory unit 303 accumulates the sleep data of the past by each user.

In addition, acetone concentration in the exhaled gas of the user on a diet tends to be high. Therefore, in a case where the comparison result of the sleeping user identification information received from the sleep data measurement device 2 and the sleeping user identification information in the past turns out to be equal or larger than the preset difference, the sleep data analysis unit 302 determines whether the acetone concentration is higher than the prescribed threshold value or not. In a case where the sleep data analysis unit 302 determines the acetone concentration is higher than the prescribed threshold value, the sleep data analysis unit 302 determines that the acetone concentration is data of the user on a diet, and may alter the determination criteria and conduct determination. For example, the threshold value of the acetone concentration in the exhaled gas is preset at 5 percent, and when the acetone concentration exceeds 5 percent, the sleep data analysis unit 302 recognizes the user, even on a diet, as the identical person.

Next, a process in which the vehicle 3 acquires driving user identification information when the user drives the vehicle 3 will be described.

The user information input unit 204 acquires information used to identify the user, based on the operation by the user at the time of initial registration for the first time use of the user identification information input device 30. For example, the user information input unit 204 acquires information such as name, age or the like which are input based on the operation by the user at the time of initial registration for the first time use of the user identification information input device 30. Also, for example, the user information input unit 204 acquires sex information used to enhance the precision of identification of the user by blood pressure, based on the operation by the user at the time of initial registration for the first time use of the user identification information input device 30. Also for example, the user information input unit 204 acquires height information used to calculate the body mass index. The user information input unit 204 is, for example, a touch panel, keyboard, or the like.

Once the user completes the initial registration for the first time use of the sleep data measurement device 2, when the user drives the vehicle 3, the user prepare so that the vehicle 3 acquires the driving user identification information by such was as wearing each of the driving user identification information acquisition unit 202, or sitting on a seat including the driving user identification information acquisition unit 202.

Also, when the user drives the vehicle 3, the driving user identification information acquisition unit 202 included in the vehicle 3 acquires the driving user identification information (Step S9). For example, right before the user drives the vehicle 3, the blood pressure measurement unit 202a measures the blood pressure, which is one of body characteristics of the user, as the driving user identification information. Also, when the user drives the vehicle 3, the body temperature measurement unit 202b measures the body temperature of the user. Also, the body weight measurement unit 202c measures the body weight of the user, which is one of body characteristics of the user, as the driving user identification information. Also, the body composition measurement unit 202d measures body composition, which is one of body characteristics of the user, as the driving user identification information based on the bioelectrical impedance of the user measured by the bioelectrical impedance measurement unit 202f. Also, the body mass index measurement unit 202e calculates the body mass index of the user, which is one of body characteristics of the user, as the driving user identification information based on the body weight and the height of the user.

Also, the acetone concentration measurement unit 202g measures the acetone concentration contained in the exhaled gas of the user, which is one of body characteristics of the user, as the driving user identification information.

The driving user identification information acquisition unit 202, upon acquiring the driving user identification information, transmits the acquired driving user identification information to the server 4 via communication unit 301 (Step S10).

In addition, the driving user identification information acquisition unit 202 may use finger print voice print, or the like of the user, which is one of body characteristics of the user, as the driving user identification information.

Next, a process in which the server 4 determines whether the user's sleep is sufficient or not for the user to drive will be described.

The acquired data within predetermined duration identification unit 304 included in the server 4 receives the driving user identification information from the vehicle 3 via communication unit 301 by the process of Step S10 (Step S11). The acquired data within predetermined duration identification unit 304 reads out the sleeping user identification information in the data table TBL 1 corresponding to the each user from the memory unit 303. And, the acquired data within predetermined duration identification unit 304 compares each of the driving user identification information received, and the sleeping user identification information in the data table TBL 1 which was read out. And, the acquired data within predetermined duration identification unit 304 determines whether the comparison result between the driving user identification information and the sleeping user identification information fall within the preset difference for each of blood pressure, body temperature, body weight, body composition (body fat, visceral fat, subcutaneous fat, muscle, bone, body water and other components within body), body mass index, bioelectrical impedance and acetone concentration in the exhaled gas (Step S12).

Also, in a case where the acquired data within predetermined duration identification unit 304 determines that the comparison result between the driving user identification information and the sleeping user identification information does not fall within the preset difference for each of blood pressure, body temperature, body weight, body composition (body fat, visceral fat, subcutaneous fat, muscle, bone, body water and other components within body), body mass index, bioelectrical impedance and acetone concentration in the exhaled gas (Step S12, NO), the acquired data within predetermined duration identification unit 304 determines that there is no data table TBL 1 of the identical user. And the server 4 waits for receiving next data from the sleep data measurement device 2 and the vehicle 3 (Step S13).

Also, in a case where the acquired data within predetermined duration identification unit 304 determines that the comparison result between the driving user identification information and the sleeping user identification information falls within the preset difference for each of blood pressure, body temperature, body weight, body composition (body fat, visceral fat, subcutaneous fat, muscle, bone, body water and other components within body), body mass index, bioelectrical impedance and acetone concentration in the exhaled gas (Step S12, YES), the acquired data within predetermined duration identification unit 304 determines that the user corresponding to the data table TBL 1 used for that determination is the identical user. In addition, the acquired data within predetermined duration identification unit 304 identifies the sleep data within the past predetermined duration as the acquired data within predetermined duration among the sleep data in the data table TBL 1 of the user which is determined to be identical, based on the time data of the sleep data (Step S14). For example, the acquired data within predetermined duration identification unit 304 identifies the sleep data 3, 4 and 5 which is sleep data within the past 24 hours as the acquired data within predetermined duration among the sleep data in the data table TBL 1 shown in FIG. 5 of the user which is determined to be identical.

The acquired data within predetermined duration identification unit 304 outputs acquisition within predetermined duration alarm information indicating the identified acquired data within predetermined duration (hereinafter "acquisition within predetermined duration alarm information"), to the sleep shortage determination unit 305.

Once the acquisition within predetermined duration alarm information is input from the acquired data within predetermined duration identification unit 304, the sleep shortage determination unit 305 reads out data, which the acquisition within predetermined duration alarm information which was input indicates, from the memory unit 303. And, the sleep shortage determination unit 305, among the data read out, calculates the total sleep time of the sleep data with the sufficient sleep flag (Step S15). For example, in a case where the sleep shortage determination unit 305 reads out data 3, 4 and 5 as data the acquisition within predetermined duration alarm information being input indicates, the sleep shortage determination unit 305 calculates total of the sleep time of the sleep data 3 and 4 with the sufficient sleep flag.

Also, the sleep shortage determination unit 305 determines whether the total calculated sleep time is equal or more than prescribed time to determine that the user's sleep is sufficient and whether the user may drive or not (Step S16). In a case where the sleep shortage determination unit 305 determines the total calculated sleep time is equal or more than prescribed time (Step S16, YES), the sleep shortage determination unit 305 determines the user may drive, and the sleep shortage determination unit 305 transmits driving permission information indicating that the user's sleep is sufficient to the vehicle 3 via the communication unit 301 (Step S17).

Also, in a case where the sleep shortage determination unit 305 determines the total calculated sleep time is shorter than prescribed time (Step S16, NO), the sleep shortage determination unit 305 determines that the user's sleep is insufficient, and the user may not drive. In addition, the sleep shortage determination unit 305 transmits driving non-permission information indicating that the user's sleep is insufficient and the user may not drive to the vehicle 3 via the communication unit 301 (Step S18).

Next, a process which the vehicle 3 conducts in case where the user's sleep is sufficient and a process which the vehicle 3 conducts in case where the user's sleep is insufficient will be described.

In case the server 4 conducts the process of the Step S17, the control unit 203 included in the vehicle 3 receives the driving permission information from the server 4 via the communication unit 201. In this case, the control unit 203 controls so that the user can drive the vehicle 3 (Step S19). For example, the control unit 203 controls so that all the operations in the vehicle 3 be accepted.

Also, in case the server 4 conducts the process of the Step 18, the control unit 203 receives the driving non-permission information from the server 4 via the communication unit 201. In this case, the control unit 203 controls so that the user cannot drive the vehicle 3 (StepS20). For example, the control unit 203 controls so that power source of the vehicle 3 does not operate, or controls so that all the operations in the vehicle 3 should not be accepted.

As above, the processes of the safe driving management system 1 according to an embodiment of the present invention are described. According to the above-mentioned safe driving management system 1 with the sleep shortage determination device 5 and vehicle 3, the sleep shortage determination device 5 includes the sleep shortage determination unit 305. The sleep shortage determination unit 305 compares sufficient sleep data containing at least one of either the respiration or the pulses of a case where the sleep of the driver is sufficient, and acquired data within predetermined duration, containing at least one of either respiration or pulses, identical to the sufficient sleep data measured within predetermined duration in the past from the time when the driver boards the vehicle 3. And, in a case where the difference between the sufficient sleep data and the acquired data within predetermined duration is equal or greater than the prescribed difference, the sleep shortage determination unit 305 determines that the driver is in sleep shortage.

In this way, the safe driving management system 1 can determine the sleep shortage before the user drives the vehicle 3.

Also, the acquired data within predetermined duration identification unit 304 identifies the acquired data within predetermined duration of the driver, based on the measurement information of the body of the driver, measured at the time when at least one of either the respiration or the pulses associated with at least either one of the respiration or the pulses contained in the sufficient sleep data, and the measurement information of the body of the driver, measured at the time when the driver boards the vehicle 3 to start driving.

In this way, the safe driving management system 1 can recognize the user before the user drives the vehicle 3 and prohibit the user in sleep shortage from driving.

Also, the acquired data within predetermined duration identification unit 304 uses blood pressure, body temperature, body weight, body composition (body fat, visceral fat, subcutaneous fat, muscle, bone, body water and other components within body), body mass index, bioelectrical impedance, the acetone concentration in the exhaled gas, etc. of the user as body characteristics.

In this way, the safe driving management system 1, by making the variety of body characteristics wider, enhances accuracy of the user identification.

Also, in a case where the sleep shortage determination unit 305 determines the sleep of the driver is insufficient; the control unit 203 controls the vehicle 3 so that the driver cannot drive the vehicle 3.

In this way, in a case where the user's sleep is insufficient when the user drives the vehicle 3, the safe driving management system 1 can prohibit the user from driving the vehicle 3.

Also, in the sleep data measurement device 2, when acquiring the sleep data of the driver, the sleeping user identification information acquisition unit 103 identifies the driver based on the measurement information of the body. In the user identification information input device 30 included in the vehicle 3, when the driver drives the vehicle 3, the driving user identification information acquisition unit 202 identifies the driver based on the same sort of the measurement information of the body as the measurement information of the body, which the sleeping user identification information acquisition unit 103 used.

In this way, identification in the different places, the place where the driver sleeps and the place where the driver drives is necessary, which causes that the identical person needs to be in the different places, and makes it possible to prevent impersonations.

In addition, the processes of the safe driving management system 1 according to an embodiment of the present invention is described, though the sleep shortage determination device 5 is not limited to the one included in the server 4. The sleep shortage determination device 5, as far as it is possible to conduct communication with adequate processes, may be included in any devices included in the safe driving management system 1.

Also, the safe driving management system 1 is not limited to the one using all of blood pressure, body temperature, body weight, body composition (body fat, visceral fat, subcutaneous fat, muscle, bone, body water, and other components within body), body mass index, bioelectrical impedance, and acetone concentration in the exhaled gas as body characteristics of the user. The safe driving management system 1 may use any body characteristics as far as adequate determination process is conducted.

The sleeping user identification information acquisition unit 103 is not limited to the one included in the sleep data measurement device 2. For example, the sleeping user identification information acquisition unit 103 may be a separate device from the sleep data measurement device 2.

Also, the sleeping user identification information acquisition unit 103 may be the one which acquires the measurement information of the body of the user measured by another device via an input device. For example, the sleeping user identification information acquisition unit 103 may be the one acquires the measurement information of the body of the user by being input via a keyboard.

Also, the driving user identification information acquisition unit 202 may be the one which acquires the measurement information of the body of the user measured by another device via an input device. For example, the driving user identification information acquisition unit 202 may be the one acquires the measurement information of the body of the user by being input via a keyboard.

In addition, the memory unit in the present invention may be included in anywhere within a range where adequate transmission and receipt of information is conducted. Also, within a range where adequate transmission and receipt of information is conducted, plural of memory units may exist and each memory unit stores distributed data.

In addition, in the process flow in the embodiment of the present invention, order of the processes may counterchange within a range where the adequate process is conducted.

In addition, the embodiment of the present invention is described, and the sleep data measurement device2, the vehicle3 and the server 4 included in the above-mentioned safe driving management system 1 has computer system inside. The above-mentioned process flow is stored in the form of program in computer readable recording media. A computer reads out and executes this program, and above processes is conducted. Here, computer readable recording media includes magnetic disc, magneto-optical disc, CD-ROM, DVD-ROM, semiconductor memory, etc. Also, the computer program may be delivered to a computer by communication line so that the computer which received the delivery may be configured to execute the above-mentioned program.

Also, the above program may be for realizing only a part of above-mentioned functions.

Further, the above program may be so-called a difference file (difference program), which is capable of realizing the above-mentioned functions in combination with a program already recorded in the computer system.

The present invention has been described, using some embodiments, though these embodiments are exemplary and do not limit the scope of the invention. Also, without departing from the scope of the invention, various omission, replacement and alteration may be conducted.

The invention claimed is:

1. A safe driving management system, comprising:
a sleep data measurement device configured to measure sleep data that is data of a user during sleep;
a sleep shortage determination device configured to determine whether the user is in a sleep shortage state based on a result of comparison between first data and second data;
a user identification information input device,
wherein the first data is sleep data of a case where a user's sleep is sufficient,
wherein the second data is sleep data measured within a predetermined duration in the past from when the user gets into a vehicle to start driving, and containing data being related to a parameter that is identical with a parameter of the first data, and
wherein the sleep shortage determination device determines that the user is in the sleep shortage state, when a difference between the first data and the second data is equal or greater than a predetermined difference,
wherein the sleep data measurement device has a sleeping user identification information acquisition unit configured to identify the user based on measurement information of a body of the user when acquiring sleep data of the user, and wherein the user identification information input device has a driving user identification information acquisition unit configured to identify the user based on the same sort of measurement information of the body as the measurement information of the body, when the user drives a vehicle.

2. The safe driving management system according to claim 1,
wherein the user identification information input device has a control unit configured to control the vehicle so that the user cannot drive the vehicle, in a case where the sleep shortage determination unit determines that the user is in the sleep shortage state.

3. The safe driving management system according to claim 1,
wherein the user identification information input device has the sleep shortage determination unit.

4. A sleep shortage determination device configured to measure sleep data that is data of a user during sleep, comprising:
a sleep shortage determination unit configured to determine whether the user is in a sleep shortage state based on a result of comparison between first data and second data; and
a sleeping user identification information acquisition unit configured to identify the user based on measurement information of a body of the user when acquiring sleep data of the user,
wherein the first data is sleep data of a case where a user's sleep is sufficient,
wherein the second data is sleep data measured within a predetermined duration in the past from when the user gets into a vehicle to start driving, and containing data being related to a parameter that is identical with a parameter of the first data,
wherein the sleep shortage determination unit determines that the user is in the sleep shortage state, when a difference between the first data and the second data is equal or greater than a predetermined difference, and
wherein the user identification information input device has a driving user identification information acquisition unit configured to identify the user based on the same sort of measurement information of the body as the measurement information of the body, when the user drives a vehicle.

5. A control method of a safe driving management system, the safe driving management system comprising:
a sleep data measurement device configured to measure sleep data that is data of a user during sleep;
a sleep shortage determination device configured to determine whether the user is in a sleep shortage state based on a result of comparison between first data and second data; and
a user identification information input device,
wherein the first data is sleep data of a case where a user's sleep is sufficient,
wherein the second data is sleep data measured within a predetermined duration in the past from when the user gets into a vehicle to start driving, and containing data being related to a parameter that is identical with a parameter of the first data,
wherein the sleep shortage determination device determines that the user is in the sleep shortage state, when a difference between the first data and the second data is equal or greater than a predetermined difference,
wherein the sleep data measurement device has a sleeping user identification information acquisition unit configured to identify the user based on measurement information of a body of the user when acquiring sleep data of the user, and
wherein the user identification information input device has a driving user identification information acquisition unit configured to identify the user based on the same sort of measurement information of the body as the measurement information of the body, when the user drives a vehicle.

6. A control method,
wherein sleep data is data of a user during sleep,
wherein first data is sleep data of a case where a user's sleep is sufficient,
wherein second data is sleep data measured within a predetermined duration in the past from when the user gets into a vehicle to start driving, and containing data being related to a parameter that is identical with a parameter of the first data,
wherein a sleep shortage determination unit determines that the user is in a sleep shortage state, when a difference between the first data and the second data is equal or greater than a predetermined difference,
wherein a sleeping user identification information acquisition unit that identifies the user based on measurement information of a body of the user when acquiring sleep data of the user, and
wherein a driving user identification information acquisition unit identifies the user based on the same sort of measurement information of the body as the measurement information of the body, when the user drives a vehicle.

7. A non-transitory computer readable storage medium that stores a program configured to cause a computer to function as a sleep shortage determination means configured to determine whether the user is in a sleep shortage state based on a result of comparison between first and second data,
wherein sleep data is data of a user during sleep,
wherein the first data is sleep data of a case where a user's sleep is sufficient,
wherein the second data is sleep data measured within a predetermined duration in the past from when the user gets into a vehicle to start driving, and containing data being related to a parameter that is identical with a parameter of the first data,
wherein a sleep shortage determination means determines that the user is in the sleep shortage state, when a difference between the first data and the second data is equal or greater than a predetermined difference,
wherein a sleeping user identification information acquisition unit that identifies the user based on measurement information of a body of the user when acquiring sleep data of the user, and
wherein a driving user identification information acquisition unit identifies the user based on the same sort of measurement information of the body as the measurement information of the body, when the user drives a vehicle.

* * * * *